(12) United States Patent
Chomczynski

(10) Patent No.: US 7,727,718 B2
(45) Date of Patent: Jun. 1, 2010

(54) REAGENTS FOR STORAGE AND PREPARATION OF SAMPLES FOR DNA ANALYSIS

(75) Inventor: Piotr Chomczynski, Cincinnati, OH (US)

(73) Assignee: Molecular Research Center, Inc., Cincinnati, OH (US)

( * ) Notice: Subject to any disclaimer, the term of this patent is extended or adjusted under 35 U.S.C. 154(b) by 479 days.

(21) Appl. No.: 11/029,608

(22) Filed: Jan. 4, 2005

(65) Prior Publication Data

US 2006/0147944 A1 Jul. 6, 2006

(51) Int. Cl.
C12Q 1/68 (2006.01)
C12N 13/00 (2006.01)
C12N 1/08 (2006.01)
G01N 33/00 (2006.01)
C07H 21/04 (2006.01)

(52) U.S. Cl. .................. 435/6; 435/173.7; 435/270; 436/94; 536/23.1

(58) Field of Classification Search .................. None
See application file for complete search history.

(56) References Cited

U.S. PATENT DOCUMENTS

| 5,346,994 | A | 9/1994 | Chomczynski |
| 5,945,515 | A | 8/1999 | Chomczynski |
| 6,469,159 | B1 | 10/2002 | Belly et al. |
| 6,831,050 | B2 * | 12/2004 | Murch et al. ............... 510/280 |
| 2002/0168361 | A1 * | 11/2002 | Kelly .......................... 424/144.1 |
| 2003/0149097 | A1 * | 8/2003 | Beilfuss et al. ............. 514/456 |
| 2003/0170822 | A1 * | 9/2003 | Itoh ............................ 435/69.4 |
| 2004/0115131 | A1 * | 6/2004 | Hellerstein ................. 424/1.73 |

FOREIGN PATENT DOCUMENTS

WO     WO 8900577 A  *  1/1989

OTHER PUBLICATIONS

Ashen, N., Oellerich M. and Schutz E, "Use of two reporter dyes without interference in a single-tube rapid-cycle PCR: α1-antitrypsin genotyping by multiplex real time fluorescence PCR with the LightCycler" 2000, Clin. Chem. 46, 156-161.
Camoes I.C.G., Salles M.R., Chevitarese O., and Gomes G.C. "Influence of pH vehicle containing glycerin used with calcium hydroxide" 2003, Dental Traumatology 19, 132-138.
FTA Cards, Cat No. 10786-010, Invitrogen, Carlsbad, CA.
Joshi A.K., Baichwal V. and Ames G.F. "Rapid polymaerase chain reaction amplification using intact bacterial cells" 1991, Biotechniques 10, 42-44.
Leal-Klevezas D.S., Martinez-Vazquez I.O., Cuveas-Frenandez B. and Martinez-Soriano J.P. "Antifreeze solution improves recovery by preserving the integrity of pathogen-infected blood and other tissues" 2000, Clinical and Diagnostic Laboratory Immunology 7, 945-946.
Lin Z. and Floros J. "Protocol for genomic DNA preparation from fresh or frozen serum for PCR amplification" 2000, Biotechniques 29, 460-466.
Mercier, B. Gaucher, C. Feugeas, O. and Mazurier C. "Direct PCR from whole blood, without DNA extraction", 1990, Nucl. Acids Res. 18, 5908.
Moore, David and Dowhan, Dennis, "Purification and Concentration of DNA from Aqueous Solutions," *Current Protocols in Molecular Biology* (2002) 2.1.1-2.1.10 (2002) John Wiley & Sons, Inc.
Ohhara M, Kurosu Y. and Esumi M. "Direct PCR of whole blood and hair shafts by microwave treatment" 1994, Biotechniques 17, 726-728.
Rogers C. and Burgoyne L. "Bacterial typing" 1997, Anal. Biochem. 247, 223-227.
Rudbeck L and Dissing J "RAPID, Simple alkaline extraction of human genomic DNA from whole blood, buccal epithelial cells, semen and forensic stains for PCR" 1998, Biotechniques 25, 588-592.
Sandhu G.S., Precup J.W. and Kline B.C. "Rapid One-step characterization of recombinant vectors by direct analysis of transformed *Escherichia coli* colonies" 1989, Biotechniques 7, 689-690.
Subbarayan P.R. Sarkar M. and Ardalan B. "Isolation of genomic DNA from human blood" 2002, Biotechniques, 1231-1234.
Truett G.E., Heeger R.L., Mynatt A.A. Truett J.A., Walker J.A. and Warman M.L. "Preparation of PCR-quality mouse genomic DNA with hot sodium hydroxide and tris" 2000, Biotechniques 29, 52-54.

* cited by examiner

*Primary Examiner*—Bradley L Sisson
(74) *Attorney, Agent, or Firm*—Frost Brown Todd LLC

(57) ABSTRACT

The present invention describes reagents and methods for storing and/or processing of biological samples for direct use in PCR and other DNA applications. After storage, the preserved DNA in the samples may then be processed and analyzed by known methods, e.g., PCR. the present invention provides in one aspect, a method for simple and rapid storage and/or processing of nucleic acids, such as DNA, from various sources, including but not limited to body fluids, various solutions, cells, plants, tissues, bacterial cell lysates containing plasmids, etc. The present invention further comprises reagents and methods employing glycols at alkaline pH to process biological samples and make DNA usable in PCR without further sample purification. Accordingly, the present invention provides in one aspect, a method for simple and rapid processing of nucleic acids, such as DNA, from various sources, including but not limited to body fluids, various solutions, cells, plants, tissues, bacterial cell lysates containing plasmids, etc.

19 Claims, No Drawings

REAGENTS FOR STORAGE AND PREPARATION OF SAMPLES FOR DNA ANALYSIS

FIELD OF THE INVENTION

The present invention relates generally to reagents and methods capable for simple and effective preservation and processing of a large number of biological samples. More specifically, the invention relates to reagents and methods for storing and/or processing of biological samples for direct use in PCR and other DNA applications. The present invention further provides for reagents and methods to process biological samples and make DNA usable in PCR without sample purification.

BACKGROUND OF THE INVENTION

The growing use of polymerase chain reaction (PCR) in molecular diagnostic has made it desirable to develop reagents and methods capable of simple and effective preservation and processing of a large number of biological samples.

Traditional alkaline lysis requires the following steps: concentrating or pelleting cells diluted in growth media; centrifuging or vortexing; lysing cells with alkaline detergent; shaking and/or agitating lysate; adding neutralization buffer; filtering and/or manipulating sample to remove the flocculent mass; adding a solid phase carrier; and adding binding buffer. Additional purification steps are generally required to remove the detergents and salts as follows: addition of solid phase carriers and addition of a binding buffer.

A frequently used source in DNA diagnostic is blood although buccal swabs and tissue biopsies are also often used, especially for the cancer testing. Currently, tissue samples are stored and preserved frozen, formalin-fixed or paraffin-imbedded. The use of formalin-fixed or paraffin-imbedded samples require a multi-step process to render DNA from these samples usable for PCR. Blood storage for DNA diagnostic purposes requires refrigeration, freeze-drying or freezing. Alternatively, blood samples are applied to a card, such as an FTA CARD (Invitrogen) and store dry at room temperature.

Leal-Klevez et al. developed a method for storing blood and tissue samples at −20 C in 20% ethylene glycol-propylene glycol aqueous solution. In this protocol, DNA can be extracted from the stored sample by the proteinase K-phenol extraction procedure.

U.S. Pat. No. 6,602,718 describes methods and reagents for stabilizing RNA and DNA in biological samples using an aqueous solution or dispersion of cationic detergent supplemented with additives including chaotropic salts, at a pH range from about 2 to about 12.

Various methods of sample processing have been used to prepare DNA for the PCR analysis. DNA is typically extracted using phenol-based methods, salt-alcohol precipitation method or adsorption on column methods. A review of these methods is provided in Current Protocols pp. 2.0.1-2.4.5. Also, U.S. Pat. Nos. 5,346,994 and 5,945,515 described reagents and methods for DNA isolation. These reagents and methods provide substantially pure DNA. However, these are time consuming and not easy adaptable for automation. Methods for performing PCR on samples without prior isolation of DNA have been developed such as: heating samples at 94° C. (Mercier et al.), microwave irradiation (Ohhara et al.) and treatment with thermophilic protease (Belly et al.). Many of these methods relay on 40 cycle-PCR amplification.

A 40-cycle PCR amplification is prone to artifacts and cannot be reliably used for diagnostic purposes.

Previously, alkaline lysis was used to prepare blood and other samples directly for PCR, without purification of DNA. Rudbeck et al. used 0.2 M NaOH to lyse at room temperature whole blood, semen and epithelial cells. The lysate was neutralized and used directly for PCR 20 mM NaOH was not effective in releasing DNA usable for PCR. Ashen et al. modified this protocol by first isolating blood leukocytes by centrifugation and lysing. The isolated leukocytes were lysed in 0.2 M NaOH at room temperature. The lysate was neutralized and used for PCR.

Truett et al. used 25 mM NaOH-0.2 mM disodium EDTA buffer, pH 12 to lyse mouse tissue samples by heating at 95 C. After heating, sample lysates were neutralized and used for PCR. This method was not very effective since it involved 40 cycles of PCR to amplify DNA fragments. Also, neutralization of the alkaline lysate added one step to the protocol and made strict requirements for accurate determination of pH in the lysate.

Lin et al. described preparation of DNA from blood by first removing hemoglobin from the whole blood by clotting the blood for a minimum 2 h followed by overnight storage and centrifugation. Resulted serum was subjected to lysis in 18 mM KOH at 37 C, neutralized and used for PCR.

Rapid protocols for DNA analysis by PCR were also detailed for bacteria. Sandhu et al. boiled bacteria colonies in water. Joshi et al. used bacteria directly for PCR without boiling. An FTA CARD method for storing and processing of bacterial cells were also reported (Rogers et al.).

There is now a need for a reliable and shelf-stable reagents and methods for the ambient temperature storage and which are compatible with reagents and methods for processing biological samples for direct PCR. Unexpectedly, it has now been found that reagents comprised of glycols preserve DNA and secure long-term ambient temperature storage of biological samples.

SUMMARY OF THE INVENTION

The present invention describes reagents and methods for storing and/or processing of biological samples for direct use in PCR and other DNA applications. After storage, the preserved DNA in the samples may then be processed and analyzed by known methods, e.g., PCR.

In the methods below, nucleic acids are preserved and processed in the presence of certain concentrations of polyalkylene glycol. Accordingly, the present invention provides in one aspect, a method for simple and rapid storage and/or processing of nucleic acids, such as DNA, from various sources, including but not limited to body fluids, various solutions, cells, plants, tissues, bacterial cell lysates containing plasmids, etc. The following is a description of the present invention with reference to nucleic acids as exemplified by DNA.

The present invention further comprises reagents and methods employing glycols at alkaline pH to process biological samples and make DNA usable in PCR without further sample purification. Accordingly, the present invention provides in one aspect, a method for simple and rapid processing of nucleic acids, such as DNA, from various sources, including but not limited to body fluids, various solutions, cells, plants, tissues, bacterial cell lysates containing plasmids, etc.

Generally, a variety of polyalkylene glycols are useful in the present invention including, for example, polyethylene glycol and polypropylene glycol. In one embodiment, the polyalkylene glycol is polyethylene glycol. Generally, the polyalkylene concentration will depend on the polyalkylene used. Depending on the weight range of polyethylene glycol used, the concentration can be adjusted.

Generally, for methods in which polyethylene glycol is used, the concentration in the Storage Reagent will be adjusted to about 25% to about 100% of the final volume. In another embodiment, the concentration of the polyethylene glycol is about 30% of the final volume.

In one embodiment, the DNA stays in a soluble form in a solution containing the storage or processing reagents.

In one embodiment, PEG and PEG derivatives are added to a PCR mix to inhibit the effect of impurities on PCR. In one embodiment, the concentration of PEG is less than about 15%. In another embodiment, the amount of PEG is from about 0.1% to about 10%.

Glycol compounds useful in the present invention include ethylene glycol, polyethylene glycols, polyglycol, propylene glycol, polypropylene glycol and glycol derivatives including polyoxyethylene lauryl ether (BRIJ®35), octylphenol-polyethylene glycol ether (Triton® X-100) and polyoxyethylene cetyl ether (BRIJ®52).

In one embodiment, the present invention provides for the combination of glycol compounds and alkaline pH (alkali) effectively lyse biological samples and inactivate PCR inhibitors. This makes it possible to use the resulting lysates directly for PCR without purification. Biological samples can be processed by the reagents and methods of the current invention at temperatures ranging form about 0 C to about 100 C.

In one embodiment, the temperature is ambient temperature ranging from about 10 C to 45 C. In another embodiment, the temperature is ambient temperature ranging from about 15 C to 35 C. In another embodiment, the temperature is ambient temperature ranging from about 18 C to 30 C. The alkaline pH used to process sample by the reagents and methods of the current invention is generally a pH from about 9 to pH about 14. In one embodiment, the pH range for sample processing at ambient temperature is from about 10 to pH about 13. In another embodiment, the pH range for sample processing at ambient temperature is from about 11 to pH about 12.5.

The biological sample can be any material composed of or containing any material of biological origin. Samples may include but are not limited to human and animal tissues, blood, bone, skin, hair, plant leaves, seeds, shoots and stalks, bacterial and cell cultures, formalin-fixed tissue, blood spotted on preservative papers or solid matrices (such as FTA paper from Whatman), and the like. The sample need not contain only the biological material. The sample may also consist of a biological material on or in a physical matrix such as a stain of a bodily fluid on a piece of fabric, a piece of tissue embedded in a piece of wood, or a scraping of dirt containing a hair fragment.

The invention is advantageously amenable to automation. The various reactants and components required to perform the method of the invention may conveniently be supplied in kit form. Such kits represent a further aspect of the invention. At its simplest, this aspect of the invention provides a kit for storage of nucleic acids from a sample comprising one or more glycols. The invention also provides a kit for processing of nucleic acids from a sample comprising an alkali and one or more glycols. Optionally included in such kits may be buffers, salts, lysis agents, e.g., proteinases, chelating agents and reducing agents.

The present invention also contemplates a reagent system, typically in kit form, that can be utilized in carrying out the before-described methods. The system includes, in an amount sufficient for at least one storage and/or processing, a separately packaged reagent for the storage and/or processing of nucleic acids in a biological sample. Instructions for use of the packaged reagent are also typically included.

The compositions of the present invention can be used for the automation of the storage and/or processing procedures in that it has long-term stability and so may be used in automatic equipment in which reagents are stored and dispensed as necessary to perform the storage and/or processing steps. In that case, a sealed package useful in an automated procedure for storage and/or processing DNA from biological samples containing the disclosed stable compositions may be provided.

DETAILED DESCRIPTION OF THE INVENTION

The present invention provides compositions, methods, and kits for storage of samples and preservation of DNA from a biological sample. Generally, the reagents comprise a glycol and a water-soluble organic solvent or mix of solvents. Unexpectedly, glycol compounds alone are sufficient to preserve DNA in biological samples stored at ambient temperatures for months. The invention provides novel reagents that extract DNA from biological samples with high efficiency without the need for toxic organic chemicals. The invention also provides methods and kits for purifying DNA that include the novel reagents.

The water-soluble organic solvents comprise lower alcohols. Alcohols are meant in the sense of the commonly used terminology for alcohol, preferably lower alcohols with 1 to 10 carbon atoms. In one embodiment, the lower alcohol is selected from methanol, ethanol, iso-propanol, n-propanol, or t-butanol, as well as glycerol, propylene glycol, ethylene glycol, polypropylene glycol, and polyethylene glycol, and mixtures thereof. In another embodiment, the alcohol is selected from the group consisting of methanol, ethanol, iso-propanol and 2-propanol. In another embodiment, ethanol, iso-propanol or a derivative or mixture thereof.

Appropriate alcohol (e.g., ethanol, isopropanol) concentrations (final concentrations) for use in the methods of the present invention are from about 25% to about 75%; from about 40% to about 60%; from about 45% to about 55%; and from about 50% to about 54%.

Appropriate polyalkylene glycols include polyethylene glycol (PEG) and polypropylene glycol. Suitable PEG can be obtained from Spectrum Laboratory Products, Inc, (Gardena, Calif., Molecular weight 200, Catalog number PO 107). The molecular weight of the polyethylene glycol (PEG) can range from about 200 to about 10,000. In a particular embodiment, PEG with a molecular weight of about 200 is used. In one embodiment, the PEG concentration is from about 0.5% to about 20%. In other embodiments, the PEG concentration ranges from about 0.1% to about 10%; from about 25% to about 100%.

"Polyethylene glycols" or "PEGs" useful in the present invention are commercially available diols having a molecular weight of from 200 to 10,000 daltons, and more preferably about 200-300 daltons. The use of PEG having other molecular weight constraints, for example higher than 10,000 daltons, is also contemplated for use in the compositions and methods of the present invention, although perhaps not as effective at providing a high yield/quality product.

In one embodiment, the glycol compounds of this invention comprise: 1,2-propanediol, 1,3-butanediol, 1,4-butanediol, 1,4-cyclohexanedimethanol-, 1,6-hexanediol, butylene glycol, diethylene glycol, dipropylene glycol, ethylene and propylene glycol (including ethylene and propylene glycol monomers and polymers, e.g., low molecular weight (less than 600) polyethylene glycols and low molecular weight (less than 600) polypropylene glycols), glycerol, long chain PEG 8000 (about 180 ethylene monomers), methyl propanediol, methyl propylene glycol, neopentyl glycol, octylphenol-polyethylene glycol ether (Triton® X-100), PEG-4 through PEG-100 and PPG-9 through PPG-34, pentylene glycol, polyethylene glycol 200 (PEG 200 about 4 ethylene monomers), polyethylene glycols, polyglycol, polyoxyethylene cethyl ether and octyl-polyethylene glycol ether, polyoxyethylene cetyl ether (BRIJ®52), polyoxyethylene lauryl ether (BRIJ ®35), polypropylene glycols, tetraethylene glycol, triethylene glycol, trimethylpropanediol, tripropylene glycol.

In another embodiment, the glycol compounds of this invention comprise: ethylene glycol, propylene glycol, polyethylene glycols, polypropylene glycols, polyglycol and glycol derivatives including polyoxyethylene lauryl ether (BRIJ ®35), octylphenol-polyethylene glycol ether (Triton® X-100) and polyoxyethylene cetyl ether (BRIJ®52). The preferred organic solvents of this invention are polyethylene glycols and glycols derivatives. The most preferred solvents are polyethylene glycols.

Storage Reagents

The Storage Reagents of the present invention preserve DNA in biological samples stored at temperatures ranging from about −80 C to about 50 C. The preferential storage of biological samples in the present invention is at ambient temperature (18-25 C.). The Storage Reagents of the present invention make possible to store biological samples at ambient temperature for several months. A biological sample used with these reagents can be any solid matter or fluid derived from/or containing biological material. Whole blood, biological fluids or tissue fragments all can be stored in the Storage Reagents of the present invention.

Under the storage conditions of the current invention, DNA can be preserved either in the double- or single-strand form for greater than several days to greater than several months. In one embodiment, the compositions are stable for at least 30 days at about 25° C. In one embodiment, the compositions are stable for at least 60 days at about 25° C. In one embodiment, the compositions are stable for at least 90 days at about 25° C.

For sample storage and DNA preservation, the Storage Reagents can be added to a solid or fluid biological sample to approach final concentration of the reagents ranging from about 25% up to about 100%. The Storage Reagents can be used as non-aqueous reagents or as water containing solutions or dispersions.

The reagents of the present invention alone are sufficient to preserve DNA for several months at room temperature. In addition, they can also comprise additives such salts, chelating agents and detergents, which facilitate solubilization of DNA and inactivation of PCR inhibitors. These additives can be added to the Storage Reagents either as dispersions or aqueous or nonaqueous solution.

The Storage Reagents can also comprise an alkaline additive. The alkaline additive can be in sufficient quantity to secure pH of a stored sample above about pH 8, 9, 10, 11, 12 or 13, with a maximum up to about pH 13.8. An alkaline additive facilitates solubility of DNA in Storage Reagents.

The unexpected feature of the present invention is that DNA is substantially soluble in the alkaline Storage Reagents with the concentrations of an organic solvent up to about 75%. Lower alcohols and polyethylene glycols have been used to precipitate DNA and RNA. The solubility of DNA in the reagents of the present invention makes it possible to take aliquot of a sample and store the rest for subsequent analysis, if necessary. The reagents and methods of the previous patent '718 relay on precipitation of DNA in stored samples. This makes difficult to take an aliquot and requires processing of the whole sample for a DNA analysis.

In one embodiment, the DNA stays in a substantially soluble form in the Storage Solution. In one embodiment, the DNA stays in a stable, substantially soluble form in the Storage Solution wherein the Storage Solution contains a high PEG concentration.

As used herein, "substantially soluble form" means that the nucleic acids remain in a stable form wherein at least about 60%, 70%, 80%, 90%, 95%, 98%, 99%, or more remains in solution without precipitating.

At pH 10 or higher alkaline additive denatures and inactivates proteins, dissociate protein-DNA complexes, hydrolyzes RNA and thus decreases or abolishes infectiveness of biological fluids used for analysis of DNA. An organic or inorganic base or mix of bases can be used as an alkaline additive in the present invention. Examples include sodium hydroxide, potassium hydroxide, ammonium hydroxide, tetramethylguanidine and trooctylamine. The skilled artisan will recognize that other strong bases may be used in place of these bases. When samples are stored with Storage Reagents at pH below 10 the DNA is preserved in a double strand form. At pH higher than about 10 DNA dissociates into a single strand form.

In one embodiment, the final concentration of alkali in the mixture prepared herein ranges from about 10 to about 90 mM. In one embodiment, the method involves forming a mixture of 1 part by volume of serum or plasma with about 4 parts by volume of an storage solution of about 20 mM alkali.

The Storage Reagents can further comprise salt or mix of salts. The storage reagent of claim 1 further comprising salt or mix of salts at concentration ranging from about 1 mM to about 0.8 M.

Generally, the salt is selected from a group containing acetate, lactate, citrate, ethylenediamine, phosphate, nitrate, sulphate and chloride salts of lithium, sodium, potassium and ammonium. In one embodiment, suitable salts include one or more of sodium chloride (NaCl), lithium chloride (LiCl), barium chloride ($BaCl_2$), potassium (KCl), calcium chloride ($CaCl_2$), magnesium chloride ($MgCl_2$), ammonium chloride ($NH_4Cl$, $NH_4SO_4$), and cesium chloride (CsCl). In one embodiment, sodium chloride is used. In general, the presence of salt functions to minimize the negative charge repulsion of the nucleic acid molecules. The wide range of salts suitable for use in the method indicates that many other salts can also be used and suitable levels can be empirically determined by one of ordinary skill in the art. The salt concentration can be from about 0.1M to about 5M; from about 0.15M to about 4M; and from about 0.2M to about 1M.

The Storage Reagents can further comprise a non-ionic agent. In one embodiment, the non-ionic agent is selected from the group consisting of Brij surfactants, oleyl surfactants; Igepal CO-990, Tween 20, Tween 40, Tween 60, Tween 80, Triton X-405, Triton X-100, Tetronic 908, Cholesterol PEG 900, Polyoxyethylene Ether W-1; Span 20, Span 40, Span 85, azones and mixtures thereof. In another embodiment, the non-ionic agent is Brij surfactant selected from the group consisting of Brij 30, Brij 35, Brij 36, Brij 52, Brij 56, Brij 58, Brij 72, Brij 76, Brij 78, Brij 92, Brij 96, Brij 97, Brij 98, Brij 98/99, and combinations thereof. In another embodiment, the non-ionic agent is Brij surfactant is Brij 35 or Brij 52.

Further, it is envisioned that other constituents can be included in embodiments of the storage solution, for example, a chaotropic salt at concentrations of between 50 mM and 6M, and preferably between 200 mM and 400 mM, can be included in the solution.

The salt or mix of salts in the Storage Reagents may constitute a buffer maintaining pH of the reagent in range from pH about 2 to pH about 13.8. In general, the addition of salt stabilizes the DNA and helps maintain double-stranded structure of DNA.

The reagents and methods of the current invention can be used to store and preserve DNA in solid and fluid biological samples including samples of human, animal, plant, fungi, yeasts and bacterial origin. The preserved DNA can be used in a variety of DNA analyses comprising medical, pharmaceutical, forensic, diagnostic or scientific purposes. The analyses after storage include PCR, hybridization, single-strand conformational polymorphism, restriction fragment length polymorphism and DNA sequencing.

The conditions during these methods are not critical. Mixing can be done by any convenient means, including for example simple agitation by stirring or vortexing. Also, if desired, higher or lower temperatures may be used, but are not necessary.

Processing Reagents

The present invention also provides for reagents and methods for processing biological samples for use in PCR directly without purification. These Processing Reagents and Methods are compatible with the Storage Reagents and Methods of the current invention. Unexpectedly, a short 3-5 minute ambient temperature incubation of a biological sample with Processing Reagents results in lysis of sample, release of DNA and inactivation of PCR inhibitors, sufficient to use aliquot of the sample directly for PCR, without purification. Some samples require 3-10 minutes heating at temperatures ranging from about 80 C to about 100 C.

The sample Processing Reagents and Methods of the current invention employ an alkaline lysis of samples performed in the presence of glycols or glycol derivatives. Glycols and glycol derivatives used in the current invention comprise propylene glycol, polyethylene glycols, polypropylene glycols, polyglycol and glycol derivatives including polyoxyethylene lauryl ether (BRIJ ®35), octylphenol-polyethylene glycol ether (Triton® X-100) and polyoxyethylene cetyl ether (BRIJ®52). The preferred Processing Reagents of this invention are polyethylene glycols and polyethylene glycol derivatives. The most preferred Processing Reagents are polyethylene glycols.

The concentration of glycols in the Processing Reagents ranges from about 25% to about 100%. In one embodiment the concentration of glycols in Processing Reagents is from about 50% to about 70%.

Biological samples can be processed for use in PCR by the reagents and methods of the current invention at temperatures ranging form about 0° C. to about 100° C. In one embodiment, the temperature is ambient temperature ranging from about 10° C. to 45° C. In another embodiment, the temperature is ambient temperature ranging from about 15° C. to 35° C. In another embodiment, the temperature is ambient temperature ranging from about 18° C. to 30° C. In another embodiment, the temperature is an ambient temperature ranging from about 18° C. to 25° C.

The alkaline pH used to process sample by the reagents and methods of the current invention is generally a pH from about 9 to pH about 13.8. In one embodiment, the pH range for sample processing at ambient temperature is from about 10 to pH about 13.5. In another embodiment, the pH range for sample processing at ambient temperature is from about 11 to pH about 13.

The Processing Reagent is strongly basic by virtue of the presence of a relatively low concentration of a base such as an alkali metal hydroxide, an alkaline earth metal hydroxide, or ammonium hydroxide. The skilled artisan will recognize that other strong bases may be used in place of these bases. The base typically is present at a final concentration of about 10 mM/L to about 0.5 M/L. In one embodiment, the base is present at a final concentration of about 10 mM/L to about 0.3 M/L. In another embodiment, the base is present at a final concentration of about 10 mM/L to about 35 mM/L. In one embodiment, the amount of alkali is sufficient to maintain alkalinity of the sample-Processing Reagent mixture above about pH 9. In another embodiment, the amount of alkali is sufficient to maintain alkalinity of the sample-Processing Reagent mixture above about pH 10. In another embodiment, the amount of alkali is sufficient to maintain alkalinity of the sample-Processing Reagent mixture above about pH 11. In another embodiment, the amount of alkali is sufficient to maintain alkalinity of the sample-Processing Reagent mixture above about pH 11.5. In another embodiment, the amount of alkali is sufficient to maintain alkalinity of the sample-Processing Reagent mixture above about pH 12.

In a typical solution according to the invention, the base is about 15 mM to about 25 mM sodium hydroxide. In the context of the present invention, a highly basic solution is a solution having a pH of at least 10, at least 11, at least 12, or at least about 13.

At this pH range most samples are effectively processed by incubation with the glycol reagents for a minimum of about 1-3 minutes at room temperature. With some samples, such as with cards with dry blood or gram-negative bacteria, require incubation at elevated temperature ranging from about 25 C up to about 100 C. In another embodiment, the incubation temperature is from about 50 C to about 90 C. In another embodiment, the incubation temperature is from about 70 C to about 90 C. After processing with the reagents of the present invention, sample lysates are ready for use in PCR without any additional steps. An aliquot of sample lysate is added to PCR mix to amplify desired DNA fragment(s). In most samples, no pH adjustment of alkaline sample lysates is necessary in the method of the present invention. This simplifies processing of samples for use in PCR and in other DNA applications.

Without wishing to be bound by theory in any way, it is believed that the absence of a need for pH adjustment in the sample processing method of the current invention is a result of an unexpected property of glycols. It is now disclosed that in alkaline aqueous solutions glycols act like a base and significantly contribute to the alkalinity of the solution. This alkaline effect of glycols is observed with propylene glycol and glycol polymers and not with ethylene glycol monomer. Triethylene glycol, polyethylene glycol 200 (PEG 200, about 4 ethylene oxide monomers), long chain polyethylene glycol 8000 (PEG 8000, about 180 ethylene oxide monomers), polyoxyethylene cetyl ether, cetylphenol-polyethylene glycol ether, and polyoxyethylene cetyl ether all exhibit the alkaline effect.

An aqueous solution containing only 20 mM KOH has pH 12.3 while the solution containing 20 mM KOH and 60% PEG 200 has pH 13.3. Similarly, 30 mM KOH has pH 12.4 and solution containing 30 mM KOH and 60% PEG 200 has pH 13.5. Thus, 60% PEG 200 causes about tenfold increase in concentration of OH ions. This alkaline effect is observed, to a various extent, with glycols including propylene glycol, polypropylene glycol, polyglycol, Brij 35, BRIJ 58 and Triton X-100. The most pronounced increase in OH concentration is observed with polyethylene glycols.

The alkaline effect of polyethylene glycol becomes significant when the pH of the aqueous solution is above about 9 and generally increases at pH above about 11. The polyethylene glycol alkaline effect is also concentration depended. For a significant pH increase, polyethylene glycol concentration should be above 10%. These properties make polyethylene glycol the preferred reagent for sample storage and processing of the present invention.

An aliquot of the polyethylene glycol-sample lysate constitutes for example 0.1 volume or less of the final volume of PCR mix. The tenfold dilution decreases polyethylene glycol concentration to below 10% and its alkaline effect is greatly diminished. Thus, the resulting PCR reaction mixture is within buffering range of a PCR buffer and no pH adjustment is necessary.

The amounts of sample lysate in the PCR mix may vary depend on the amount of DNA in the sample. Typically, the sample lysate used for PCR comprise about 0.01 ng to 200 ng. The preferred amount of DNA is ranging from about 1 ng to about 20 ng.

The alkaline effect is not observed with glycol monomer, ethylene glycol. At alkaline pH ethylene glycol acts as an acid and is not beneficial in sample processing methods of the present invention. Pentanediol and polyalcohol such as glycerin do not show the alkaline effect.

It is further disclosed in the present invention that the presence of polyethylene glycol, polyoxyethylene lauryl ether and polyoxyethylene cetyl ether during PCR makes DNA amplification less sensitive to PCR inhibitors and results in significant increase of amplification of desired DNA fragments. The preferred concentration of polyethylene glycol in the PCR mix is from about 2% to about 10% and the preferred concentration of polyoxyethylene lauryl ether and polyoxyethylene cetyl ether is from about 0.5% to about 2%.

General Procedures

The sample is added to a fixed volume of Storage Reagent. The sample is agitated so that substantially all of the sample comes into contact with the Storage Reagent. The sample in Storage Reagent can be used immediately for DNA processing or stored at ambient temperature for at least 10, 20, 30, 40, 50, 60 or more days.

Following storage, 1-50 volumes of Processing Reagent is added to the Storage Reagent containing the sample and the solution is mixed thoroughly. For DNA extraction, the Processing Solution provides the optimum pH and salt conditions for processing of the DNA.

Alternatively, a biological sample can be immersed directly in Processing Reagent and used for PCR or other DNA analysis.

As a result of the reagents and methods described herein, rapid and readily automatable methods of storing and processing genomic nucleic acid from a cell are now available. Nucleic acids processed by the disclosed methods can be used for molecular biology applications requiring nucleic acids, such as the preparation of DNA sequencing templates, microinjection, transfection or transformation of mammalian cells, in vitro synthesis of RNAi hairpins, reverse transcription cloning, cDNA library construction, PCR amplification, and gene therapy research, as well as for other applications including, but not limited to, transformation, restriction endonuclease or microarray analysis, selective RNA precipitations, in vitro transposition, separation of multiplex PCR amplification products, preparation of DNA probes and primers and detemplating protocols.

The reagents and methods described herein can be used together with a variety of nucleic acid purification techniques, including those described in U.S. Pat. Nos. 5,705,628 and 5,898,071 as well as WO 99/58664, the contents of which are herein incorporated by reference.

Biological samples, solid or fluid, including samples of human, animal, plant, yeasts, fungi, bacterial and viral origin can be mixed with reagents of the current invention for storage and/or processing. Biological fluids, including blood, can be collected under vacuum to a tube containing reagents of the current invention for storage and/or processing.

The reagents and methods of the present invention can be used for direct PCR to amplify DNA fragments with variety of DNA polymerases including Platinium® and AccuPrime™ polymerases from Invitrogen, Carlsbad. Calif., Sigma Taq from Sigma, St Louis, Mo., and Takara Ex Taq TM from Takara Bio Inc, Seta, Japan.

In one embodiment, one or more additional components may be added to the reagents. In one embodiment, one or more additional components may be added to the Storage Reagents. In one embodiment, one or more buffers, salts, stabilizing agents, lysis agents, chelating agents and/or reducing agents is added to regent mix. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

The chelating agent may be any composition that is effective for chelating metal ions. Chelating agents also provide the advantage of serving as DNAase inhibitors. Suitable chelating agents for use in the invention include, for example, disodium ethylenediaminetetraacetate (EDTA), citric acid, salicylates (e.g., sodium salicylate, 5-methoxysalicytate and homovanilate), N-acyl derivatives of collagen, laureth-9 and N-amino acyl derivatives of beta-diketones (enamines). The skilled artisan will recognize that other chelating agents may be used, alone or in combination. The chelating agent can be present at a concentration of 1-500 mM, typically 1-100 mM, and advantageously about 25 mM.

The stabilizing agent can be, for example, sodium metasilicate, sodium silicate, sodium sesquisilicate, sodium aluminosilicate, sodium fluorosilicate, and can be present at a concentration of about 1 mM to about 500 mM, typically 1-100 mM, and advantageously about 25 mM.

The buffering agent that optionally is present may be any agent that can act as a pH buffer. Such agents are well known in the art and include tetrasodium pyrophosphate, sodium citrate, sodium carbonate, trisodium nitrilotriacetic acid, sodium fluoroborate, sodium borate, and sodium triphosphate. The buffering agent can be present at a concentration of 0-500 mM, typically 1-200 mM, and advantageously at about 25-150 mM.

Optionally, in another embodiment, at least one antioxidant may be added to the solutions of the present invention. In one embodiment, he antioxidant is selected form the group consisting of BHA, BHT, octyl or dodecyl gallate, $SO_2$, for instance in the form of sodium sulfites or sodium thiosulfite, lactic acid, citric acid, tartaric acid and/or the salts thereof, vitamin C, vitamin E and uric acid and the salts thereof. Uric acid and the salts thereof are preferably added in a concentration of from about 0.01 to about 1 wt. %, vitamin C in a concentration of 0 from about 0.01 to 2 wt. %, and vitamin E in a concentration of from about 0.01 to about 0.1 wt. %.

The preservatives used may be salicylic acid salts (preferably from about 0.01 to about 0.5 wt. %), PBH ester (preferably from about 0.05 to about 0.6 wt. %), imidazolidinyl urea derivatives (preferably from about 0.01 to about 0.6 wt. %), chlorohexidine, NIPA-ESTER Registered TM or antibiotics.

In the above methods, the DNA may be alcohol- or acid-precipitated and washed with solutions known in the art to remove specific contaminants that would otherwise co-purify with the DNA. Examples of such contaminants are RNA, endotoxins, plant resins, and polyphenolic compounds. A wash solution typically comprises a low concentration of a chaotropic agent and an alcohol such as ethanol or isopropanol. For example, the wash solution may comprise 1M guanidine hydrochloride and 60% ethanol, pH 7.0. After this incubation, the DNA is recovered by centrifugation, vacuum, pumping, or any other method known in the art.

The procedure given above is not meant to be limiting as many variations are possible as may be made by those skilled in the art of purification of DNA. The present invention, thus generally described, will be understood more readily by reference to the following examples, which are provided by way of illustration and are not intended to be limiting of the present invention.

Reagent Kits

The present invention also contemplates a reagent system, typically in kit form, that can be utilized in carrying out the before-described methods. The system includes, in an amount sufficient for at least one storage and/or processing, a separately packaged reagent for the storage and/or processing of nucleic acids in a biological sample. Instructions for use of the packaged reagent are also typically included.

As used herein, the term "package" refers to a solid matrix or material such as glass, plastic, paper, foil and the like capable of holding within fixed limits reagents of the present invention. "Instructions for use" typically include a tangible expression describing the reagent concentration or at least one assay method parameter such as the relative amounts of reagent and sample to be admixed, maintenance time periods for reagent/sample admixtures, temperature, buffer conditions and the like. The packaging materials discussed herein in relation to diagnostic systems are those customarily utilized in diagnostic systems. Such materials include glass and plastic (e.g., polyethylene, polypropylene and polycarbonate) bottles, vials, plastic and plastic-foil laminated envelopes and the like.

Specifically, the invention provides a compartmentalized kit to receive, in close confinement, one or more containers which comprises: (a) a first container comprising the Storage Reagent of the present invention or the Processing Reagent of the present invention; and (b) one or more other containers comprising one or more of the following: buffer reagents, salts, alkalis, preservatives, neutralizing buffers, alcohols, sample collection tubes and instructions.

In one embodiment, the invention provides a compartmentalized kit to receive, in close confinement, one or more containers which comprises: (a) a first container comprising the Storage Reagent of the present invention; (b) a second container comprising the Processing Reagent of the present invention; and (c) one or more other containers comprising one or more of the following: buffer reagents, salts, alkalis, preservatives, neutralizing buffers, alcohols, sample collection tubes and instructions.

In some kits, it is envisioned that a plurality of tubes used in the culture of cells, for example the Lid-Bac tube (U.S. Pat. Nos. 5,958,778 and 6,503,455, incorporated herein by reference), can also be included. These tubes would allow for the culture of target cells and the storage, processing and solubilization of those same cells to be accomplished all in a single tube, using the reagents and methods of the present invention.

The skilled artisan will recognize that the solution components may be combined in different combinations and at different concentrations to achieve optimal storage and extraction of DNA from nearly any biological sample. The skilled artisan also will recognize that the salts described above, e.g., sodium, for these additives could be replaced by salts containing other suitable counterions, for example, potassium or lithium.

One skilled in this art will recognize that the above description is illustrative rather than exhaustive. Indeed, many additional formulations techniques and pharmaceutically-acceptable excipients and carrier solutions are well-known to those skilled in the art, as is the development of suitable dosing and treatment regimens for using the particular compositions described herein in a variety of treatment regimens.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned are incorporated herein by reference. Unless mentioned otherwise, the techniques employed or contemplated herein are standard methodologies well known to one of ordinary skill in the art. The materials, methods, and examples are illustrative only and not limiting.

EXAMPLES

Example 1

Human whole blood is collected to a 5 ml BD Vacutainer® containing 10.8 mg K2EDTA. 0.4 ml of whole blood aliquot is mixed with 0.8 ml of Storage Reagent containing PEG 200 and the mixture is stored at room temperature (18 C-23 C).

After 177 days of storage 5 µl aliquot of blood-PEG mixture is collected and added to 50 µl Processing Reagent containing 60% PEG 200 and 20 mM KOH. The resulting blood lysate is incubated at room temperature (24 C.) for 3 minutes and 2 µl aliquot is added to a 20 µl PCR mix. PCR is performed with Platinum® Taq polymerase kit (Invitrogen, Carlsbad Calif.) using hGAPDH primers encompassing 626 bp (GAPDH gene) and 434 bp (GAPDH pseudogene) DNA fragment. Amplification is carried on for 30 cycles at 60 C. Amplified DNA is electrophoresed in 1% agarose gel and ethidium bromide staining reveals the presence of 626 and 434 bp hGAPDH DNA fragments.

Example 2

Human whole blood is collected to a 5 ml blood Vacutainer. Five µl of blood is mixed with the Storage Reagent as in Example 1. The resulting lysate is incubated at room temperature for 5 minutes. 2 µl of the incubated lysate is added to 20 µl PCR mix/PCR is performed with Takara polymerase using primers encompassing 5 kb fragment of human beta-globin gene. Amplification is carried on for 35 cycles at 65 C. Amplified DNA is electrophoresed in 1% agarose gel and ethidium bromide staining reveals the presence of a 5 kb hGAPDH DNA fragment.

Example 3

A 0.1 ml sample of human saliva is mixed with 2 ml of Processing Reagent containing 60% PEG 200 and 20 mM KOH and stored at room temperature. After 70 days of storage 2 µl aliquot is added to 20 µl PCR mix. PCR is performed with Sigma® Taq polymerase kit (Sigma St. Louis, Mo.) using hGAPDH primers encompassing 221 bp fragment. Amplification is carried on for 35 cycles at 60 C. Amplified DNA is electrophoresed in 1% agarose gel and ethidium bromide staining reveals the presence of 221 bp hGAPDH fragment.

Example 4

Further, 56 mg of rat liver fragment are immersed in 0.5 ml of Storage Reagent containing PEG 200. After 5 weeks of storage at room temperature the fragment is dispersed with a pipette tip in 0.56 ml of the Processing reagent containing 60% PEG 200 and 16 mM KOH and is incubated for 5 minutes at 80 C. 2 µl aliquot of the resulting lysate are added to 20 µl PCR mix. PCR is performed with Sigma® Taq polymerase kit (Sigma St. Louis, Mo.) using rat GAPDH primers encompassing 221 bp fragment. Amplification is carried on for 35 cycles at 60 C. Amplified DNA is electrophoresed in 1% agarose gel and ethidium bromide staining reveals the presence of 221 bp hGAPDH fragment.

Example 5

Culture of *Micrococus luteus* is suspended in Processing Reagent containing 50% PEG 200 and 16 mM NaOH. 5 µl aliquot of the suspension, containing 0.4 ng bacterial DNA, is added to PCR mix. PCR is performed with Sigma Taq polymerase with 35 amplification cycles at 60 C using primers encompassing 700-800 DNA fragment of 16 S rRNA gene. Amplified DNA is electrophoresed in 1% agarose gel and ethidium bromide staining reveals the presence of a 700-800 bp DNA fragment.

Example 6

A 0.1 mg sample of human finger nail is incubated for 15 minutes at 88° C. with Processing Reagent containing 50% PEG 200, 16 mM KOH and 0.1% Triton X-100. 2.5 µl of the incubation mixture is added to the PCR mix. PCR is performed with Platinum Taq polymerase using hGAPDH primers encompassing 626 and 434 bp fragments. Amplification is carried on for 35 cycles at 60 C. Amplified DNA is electrophoresed in 1% agarose gel and ethidium bromide staining reveals the presence of 626 and 434 bp hGAPDH fragments.

Example 7

Chicken liver (11 mg) and chicken feather tip are incubated separately at 86 C for 15 minutes in 0.1 ml of Processing Reagent containing 50% PEG 200 and 16 mM KOH. Diluted aliquot corresponding to 0.05 µl of the liver lysate and 5 µl aliquot of the feather lysate are added to separate PCR mixes. PCR is performed with Sigma Taq polymerase using chicken beta-actin primers encompassing 202 bp fragment. 35 amplification cycles are performed at 60 C. Amplified DNA is electrophoresed in 1% agarose gel and ethidium bromide staining reveals in both processed samples the presence of 202 bp beta-actin fragment.

REFERENCES

1) Annunziata O., Asherie N., Lomakin A., Pande J., Ogun O., and Benedek G B. "Effect of polyethylene glucol on the liquid-liquid phase transition in aqueous protein solutions" 2002, Proc. Natl. Acad. Sci. 10, 14165-14170.
2) Ashen, N., Oellerich M. and Schutz E, "Use of two reporter dyes without interference in a single-tube rapid-cycle PCR: α1-antitrypsin genotyping by multiplex real time fluorescence PCR with the LightCycler" 2000, Clin. Chem. 46, 156-161.
3) Belly R. T. and Gary C. J. U.S. Pat. No. 6,469,159, October 2002.
4) Camoes I. C. G., Salles M. R., Chevitarese O., and Gomes G. C. "Influence of pH vehicle containing glycerin used with calcium hydroxide" 2003, Dental Traumatology 19, 132-138.
5) Current Protocols in Molecular Biology, pp. 2.1.1-2.4.5, F. M Ausubel et al. eds, John Wiley & Sons, Inc., New York, 2004.
6) FTA Cards, Cat no. 10786-010, Invitrogen, Carlsbad, Calif.
7) Joshi A. K., Baichwal V. and Ames G. F. "Rapid polymaerase chain reaction amplification using intact bacterial cells" 1991, Biotechniques 10, 42-44.
8) Leal-Klevezas D. S., Martinez-Vazquez I. O., Cuveas-Frenandez B. and Martinez-Soriano J. P. "Antifreeze solution improves recovery by preserving the integrity of pathogen-infected blood and other tissues" 2000, Clinical and Diagnostic Laboratory Immunology 7, 945-946.
9) Lin Z. and Floros J. "Protocol for genomic DNA preparation from fresh or frozen serum for PCR amplification" 2000, Biotechniques 29, 460-466.
10) Mercier, B. Gaucher, C. Feugeas, O. and Mazurier C. "Direct PCR from whole blood, without DNA extraction", 1990, Nucl. Acids Res. 18, 5908.
11) Ohhara M, Kurosu Y. And Esumi M. "Direct PCR of whole blood and hair shafts by microwave treatment" 1994, Biotechniques 17, 726-728.
12) Rogers C. and Burgoyne L. "Bacterial typing" 1997, Anal. Biochem. 247, 223-227.
13) Rudbeck L and Dissing J "Rapid, Simple alkaline extraction of human genomic DNA from whole blood, buccal epithelial cells, semen and forensic stains for PCR" 1998, Biotechniques 25, 588-592.
14) Sandhu G. S., Precup J. W. and Kline B. C. "Rapid One-step characterization of recombinant vectors by direct analysis of transformed *Escherichia Coli* colonies" 1989, Biotechniques 7, 689-690.
15) Subbarayan P. R. Sarkar M. and Ardalan B. "Isolation of genomic DNA from human blood" 2002, Biotechniques, 1231-1234.
16) Truett G. E., Heeger R. L., Mynatt A. A. Truett J. A., Walker J. A. and Warman M. L. "Preparation of PCR-quality mouse genomic DNA with hot sodium hydroxide and tris" 2000, Biotechniques 29, 52-54.

What is claimed is:

1. A reagent for processing a biological sample containing DNA for use in DNA analysis, comprising an amount of an alkali and a polyalkylene glycol capable of effectively lysing the sample, releasing the DNA and inactivating PCR inhibitors at ambient temperatures; wherein the polyalkylene glycol or a mix of polyalkylene glycols is at a concentration of not less than 25%; wherein the alkali is capable of maintaining the pH of the reagent from pH 12 to pH 13.8.

2. The reagent of claim 1, wherein the polyalkylene glycol is selected from the group consisting of polyethylene glycols, polypropylene glycols, polyglycol, and mixtures thereof.

3. The reagent of claim 1, wherein the alkali is selected from a group containing: sodium hydroxide, potassium hydroxide, lithium hydroxide, 1,1,3,3 tetramethylguanidine, trioctylamine, tetramethylammonium hydroxide and triethylphenylammonium hydroxide.

4. The reagent of claim 1, further comprising a detergent or mix of detergents.

5. The reagent of claim 4, wherein the detergent is a non-ionic agent selected from the group consisting of: polyoxyethylated fatty alcohol ethers, oleyl surfactants, Polyoxyethylene(100) nonylphenyl ether, Polyoxyethylene(20) sorbitan monolaurate, Polyoxyethylene(20) sorbitan monopalmitate, -Polyoxyethylene(20) sorbitan monostearate, Polyoxyethylene(20) sorbitan monooleate, -Polyoxyethylene(40) isooctylphenyl ether, Polyoxyethylene(10) isooctylphenyl ether, polyoxypropylene-polyoxyethylene ethylene diamine-based block copolymers, Cholesterol PEG 900, Polyoxyethylene 10 cetyl ether, Polyoxyethylene 20 cetyl ether, Sorbitan monolaurate, Sorbitan monopalmitate, Sorbitan trioleate, azones and mixtures thereof.

6. The reagent of claim 1, further comprising a salt at a final concentration from 1 mM to 0.8 M.

7. The reagent of claim 6, wherein the salt is selected from a group comprising: acetate, lactate, citrate, ethylenediamine, phosphate, nitrate, sulphate and chloride salts of lithium, sodium, potassium and ammonium and mixtures thereof.

8. The reagent of claim 1, further comprising water.

9. The reagent of claim 8, further comprising an organic solvent or mix of solvents.

10. The reagent of claim 9, wherein the concentration of organic solvent is from 10% to 80% lower alcohol, from 20% to 75% of at least one alkylene glycol, and from 0.05% to 10% non-ionic agent in a non-aqueous or aqueous composition.

11. A sealed package useful in an automated procedure for processing of nucleic acid from biological samples containing the reagent of claim 1.

12. A kit for storage of nucleic acids, comprising the reagent of claim 1 at suitable concentrations for processing nucleic acids from various sources for analysis.

13. The kit of claim 12, wherein the reagent comprises at least one alkylene glycol at a final concentration of from 25% to 75%.

14. The kit of claim 12, further comprising a lower alcohol at a final concentration of from about 1% to 25%.

15. The kit of claim 12, further comprising a salt.

16. A reagent for storing a biological sample containing DNA comprising: an organic solvent comprising ethylene glycol or polyethylene glycol; a lower alcohol; a polyoxyethylated fatty alcohol ether; a citrate at a final concentration from 1 mM to 0.8 M; sodium hydroxide; and water; wherein the concentration of the organic solvent is from 25% to 75%; wherein the citrate constitutes a buffer that maintains the pH of the reagent from 12 to 13.8; wherein the reagent comprises ethylene glycol at a final concentration of from 25% to 75%; and wherein the reagent is capable of effectively preserving DNA at temperatures ranging from $-80°$ C. to $50°$ C.

17. A reagent for processing a biological sample containing DNA for use in DNA analysis, comprising: ethylene glycol or polyethylene glycol at a concentration of not less than 25%; an alkali at a concentration sufficient to maintain the sample at a pH above about 11.5; a polyoxyethylated fatty alcohol ether; a citrate at a final concentration from 1 mM to 0.8M; and water; wherein the alkali is at a concentration sufficient to maintain the lysate at a pH above 11.5; and wherein the reagent is capable of effectively lysing the sample, releasing the DNA and inactivating PCR inhibitors at ambient temperatures.

18. The storage reagent of claim 1, wherein the reagent consists essentially of an amount of an alkali, water, and a polyalkylene glycol capable of effectively lysing the sample, releasing the DNA and inactivating PCR inhibitors at ambient temperatures.

19. A mixture comprising DNA and the reagent of claim 1.

* * * * *